(12) United States Patent
Wang et al.

(10) Patent No.: US 6,249,343 B1
(45) Date of Patent: Jun. 19, 2001

(54) WAVELENGTH REFERENCE STANDARD USING MULTIPLE GASES

(75) Inventors: Gary Wang; Peter Egerton; Kenneth R. Wildnauer, all of Santa Rosa, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 09/429,052

(22) Filed: Oct. 29, 1999

(51) Int. Cl.[7] .................................................. G01J 1/10
(52) U.S. Cl. .................. 356/243.1; 356/437; 356/432
(58) Field of Search .................................... 356/437, 438, 356/439, 440, 432, 243.1

(56) References Cited

U.S. PATENT DOCUMENTS

| Re. 35,355 | * 10/1996 | Ryan et al. | 356/352 |
| 5,818,598 | * 10/1998 | Kebabian | 356/434 |

OTHER PUBLICATIONS

Technical Digest—Symposium on Optical Fiber Measurements, 1992; Digest of a symposium sponsored by the National Institute of Standards and Technology in cooperation with the IEEE Lasers and Electro–Optics Society and the Optical Society of America; Sep. 15–17, 1992; pp. 191–194.

2010WR Series—Wavelength Reference Standard—Preliminary; Newport, pp. 2–18 and 2–19.

* cited by examiner

*Primary Examiner*—Frank G. Font
*Assistant Examiner*—Roy M. Punnoose
(74) *Attorney, Agent, or Firm*—Robert T. Martin

(57) ABSTRACT

Wavelength reference standard using multiple gasses and calibration methods using same. A wavelength reference using absorption lines of multiple gasses provides stable reference wavelengths over multiple regions of interest of the optical spectrum. The gasses may be in separate cells or combined in one cell. Improved calibration using the reference is achieved by performing calibration measurements at a plurality of known wavelengths and using an average calibration constant derived from the plurality of measurements. In a second embodiment, improved calibration is achieved by performing calibration measurements at a plurality of known wavelengths and calculating a higher order calibration model, such as a least-squares linear fit. Both approached may be extended by segmenting the wavelength range and using calculated calibration values for each segment.

27 Claims, 3 Drawing Sheets

WAVELENGTH REFERENCE STANDARD USING MULTIPLE GASES

BACKGROUND OF THE INVENTION

1. Field of the Invention

The present invention pertains to calibration references for use with optical wavelength measuring devices such as Optical Spectrum Analyzers. In particular it pertains to calibration references using broad band light sources coupled to gas cells providing absorption lines at known wavelengths, and methods for using them.

2. Art Background

Optical wavelength measuring devices such as Optical Spectrum Analyzers are complex eletromechanical systems. Periodic calibration is required to maintain the accuracy of such systems. To perform such calibration, references are used. A reference may be emissive, providing energy at a known wavelength or frequency, or group of wavelengths or frequencies, or it may be absorptive, coupled to a broadband source and providing absorption lines at known wavelengths or frequencies. It is understood that wavelength and frequency are reciprocals, and may be interchanged.

To be suitable as a reference, the device in question should provide a stable output in varying environmental conditions, such as temperature, humidity, and atmospheric pressure. The device must also provide a stable reference over long periods of time. The other requirement for a reference is that it cover the frequency or wavelength range of interest. References based on mechanical properties can be manufactured, but they are typically bulky, and require initial calibration and periodic recalibration, typically at the factory.

Modern optical communications systems have extended from wavelengths in the 1.5 micrometer region to the 1.6 micrometer region. What is needed is a reference which covers both the 1.5 and 1.6 micrometer regions, and one which remains stable over time.

SUMMARY OF THE INVENTION

A stable reference for calibrating optical systems is provided by filtering the light emitted from a broadband source through two gasses, providing stable absorption lines in both the 1.3 and 1.5 micrometer regions of the spectrum. The gasses may be provided in two separate cells or mixed in one cell. Calibration using the reference is performed by making a plurality of measurements at known wavelengths of the gasses, deriving a correction model from the measurements.

BRIEF DESCRIPTION OF THE DRAWINGS

The present invention is described with respect to particular exemplary embodiments thereof and reference is made to the drawings in which.

DETAILED DESCRIPTION

Periodic calibration of optical instruments such as Optical Spectrum Analyzers requires the use of a stable reference. A suitable stable reference will provide known standard wavelengths, either as emission lines or absorption lines. It is understood in the art that wavelength and frequency are reciprocals, so a suitable reference may also be referred to as a frequency standard. Such references must be stable over shifting environmental conditions, such as temperature, humidity, and atmospheric pressure. They should also provide both short term and long term stability.

In their 1992 paper, "Moderate-Accuracy Wavelength Standards for Optical Communications" printed in "Technical Digest—Symposium on Optical Fiber Measurements, 1992" NIST Special Publication 839 by the United States Department of Commerce, Gilbert et. al identify absorption lines of gasses as providing a reference of suitable stability for calibrating Optical Spectrum Analyzers. They disclose the use of acetylene ($C_2H_2$) as a suitable reference for the 1.5 micrometer portion of the spectrum, and refer experiments using methane ($CH_4$) as a reference in the 1.3 micrometer portion of the spectrum. Both the 1.5 and 1.6 micrometer portions of the spectrum are of keen interest in optical fiber based telecommunications systems.

U.S. Pat. No. 5,828,061 to Kakimoto also disclosed the use of a specific absorption line of a gas in calibrating an Optical Spectrum Analyzer.

Figure 1:
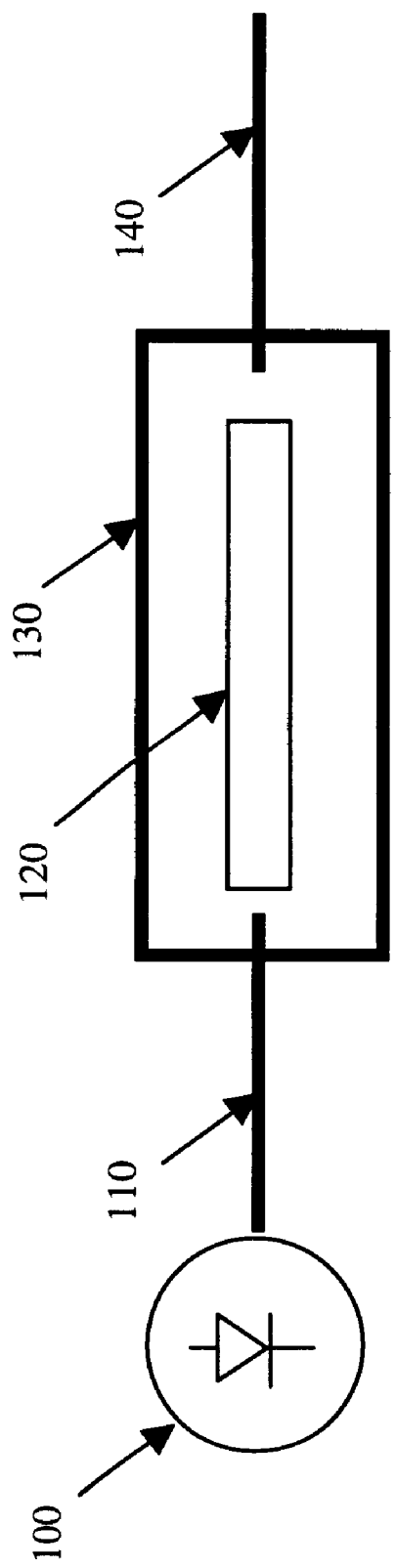
FIG. 1 shows an embodiment of the present invention.

FIG. 1 shows an embodiment of the present invention. Light source 100 provides a stable wide-band source of illumination, which is carried by fiber 110 to absorption cell 120 which contains a mixture of gasses. Separate cells for each gas could also be used. Absorption cell 120 is enclosed in container 130. Fiber 140 carries the output of the reference cell to the device under test.

Light source 100 may be a white light source, and amplified spontaneous emission (ASE) source, a light emitting diode (LED) source, or an edge-emitting light emitting diode (EELED) source. In the preferred embodiment, either a single wideband EELED, or a pair of EELEDs each optimized for a corresponding set of absorption lines are used. Suitable EELEDs are available from the Hewlett-Packard Company of Palo Alto, Calif.

In the preferred embodiment, absorption cell 120 contains a mixture of two gasses, methane and acetylene. The partial pressure of each gas determines the depth of the corresponding absorption lines. While the depth of absorption lines increases with pressure, absorption line width also increases with pressure. Absorption line depth also increases with the optical length of the cell. Increasing the optical length of the cell increases its size, the amount of the gasses used, and the overall attenuation of the light source. Increased pressure also increases overall attenuation. Partial pressures in the range of 200 to 600 Torr provide suitable absorption lines in a cell approximately 5 centimeters in length. While the preferred embodiment makes use of a single pass through the cell, a more complex cell construction providing a folded optical path could also be used. In the preferred embodiment, a partial pressure of 200 Torr for acetylene and 400 Torr for methane is used. Different gas combinations may be used for particular wavelengths of interest, and nonreactive filler gasses may also be included in the cell. For some gasses, such as acetylene, a filler such as nitrogen may be used. For a more reactive gas such as hydrogen cyanide, a noble gas such as argon is preferred.

Enclosure 130 protects absorption cell 120 from damage, allows for precision alignment of fibers 110 and 140 with absorption cell 120, blocks out stray light, and also provides a stabilizing thermal environment. If separate gas cells are used rather than one cell containing a mixture of gasses, each absorption cell may be present in its own enclosure, and connected in series with the light source. Alternatively, both absorption cells may be placed in the same enclosure, and coupled in series through the use of optical fiber, or through placing the cells along a common optical path.

A number of different gasses provide suitable absorption lines in different portions of the spectrum. If a single cell containing a gas mixture is to be used, a number of considerations must be examined in selecting a suitable mixture. First, the absorption lines of the gasses should not overlap. Second, the gas mixture should be stable over time and anticipated environmental conditions.

Suitable gasses for the 1.5 micrometer region include: acetylene, hydrogen cyanide, hydrogen iodide, and carbon monoxide. Methane is suitable for the 1.6 micrometer region, and water vapor ($H_2O$) is useful in the 1.3 micrometer region. In mixtures, other gases such as argon may be present, as long as they do not present absorption lines in spectral areas of interest.

Figure 2:
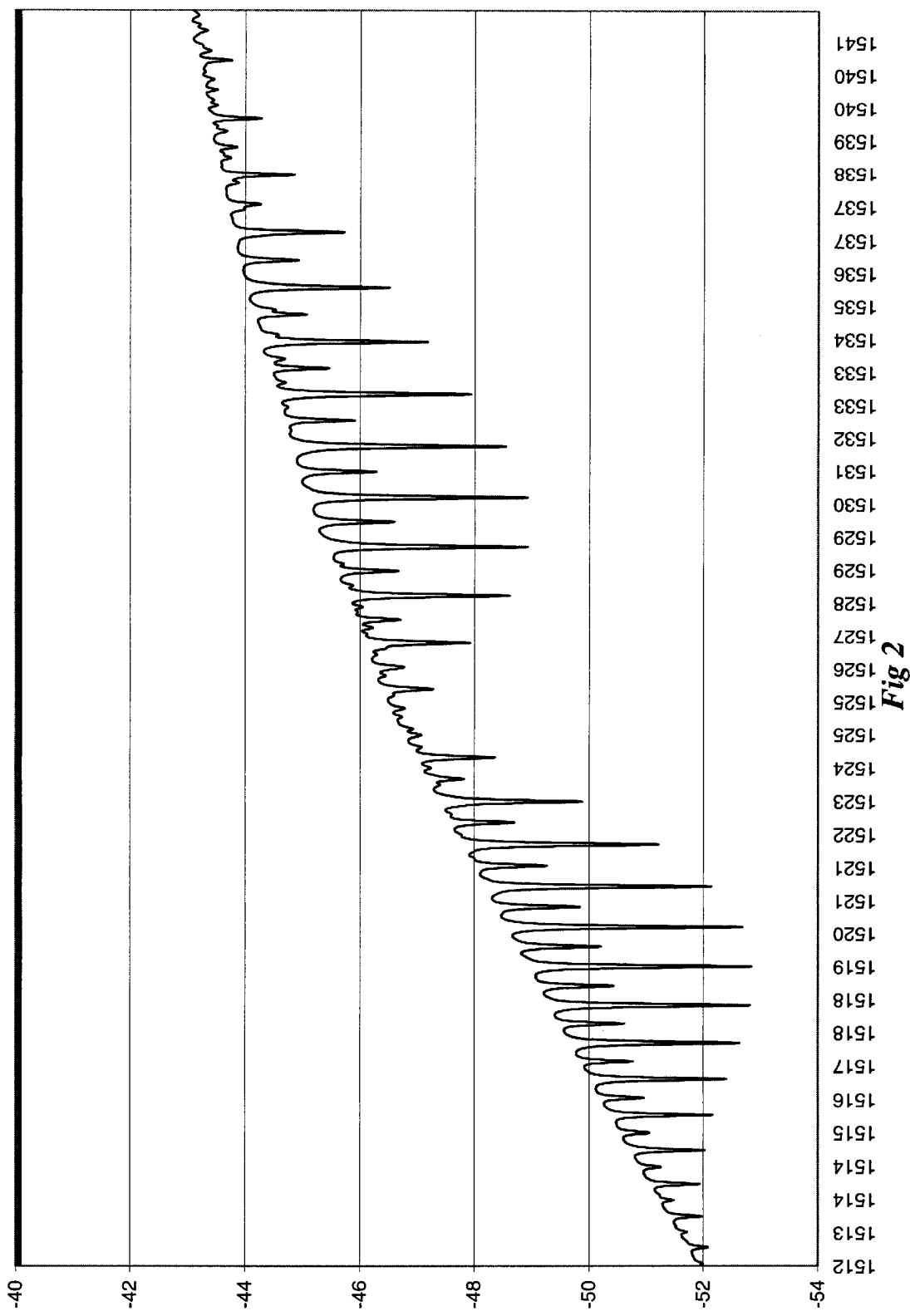
FIG. 2 shows the absorption spectrum of Acetylene ($C_2H_2$)
Figure 3:
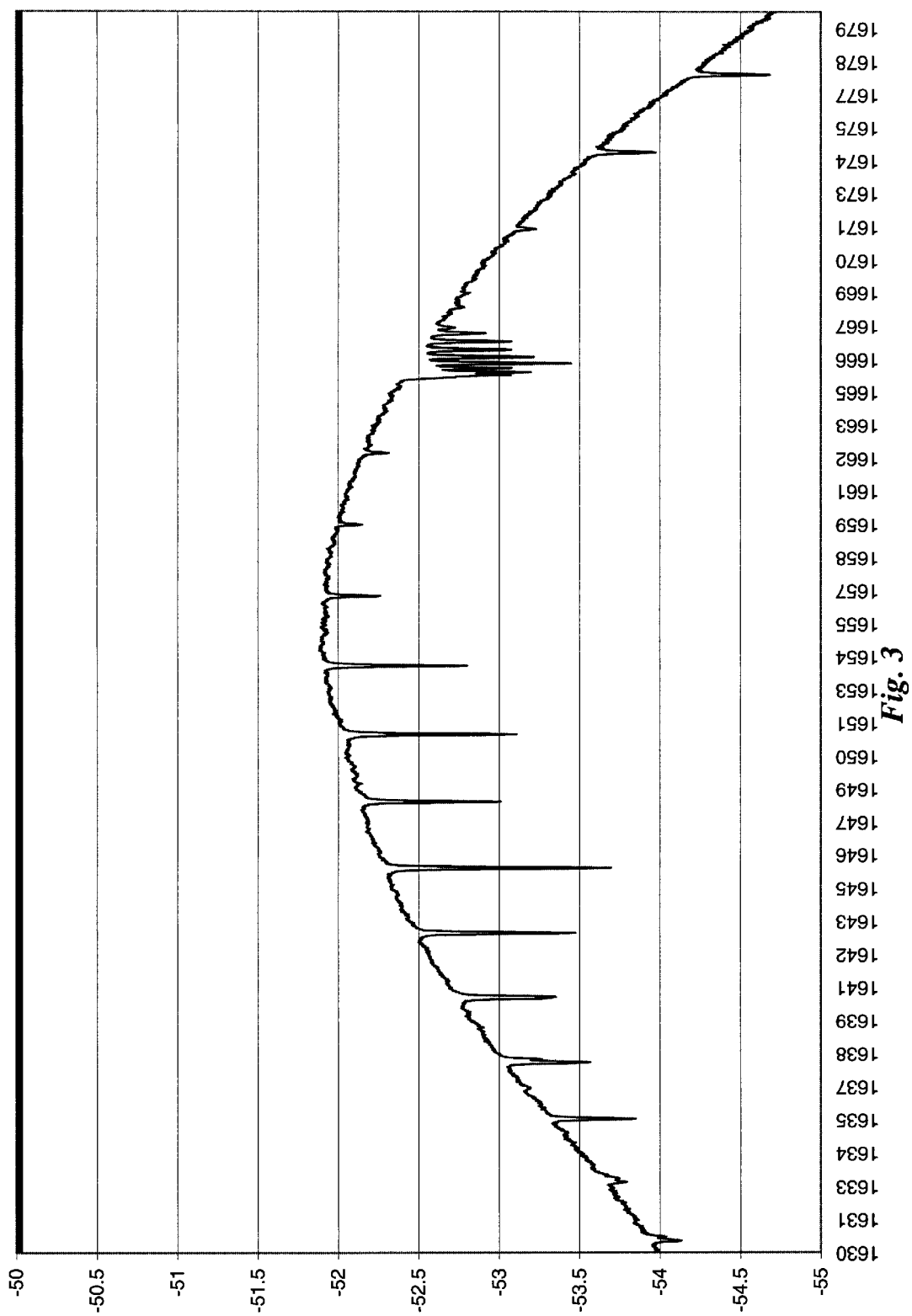
FIG. 3 shows the absorption spectrum of Methane ($CH_4$).

FIG. 2 shows the absorption spectrum of acetylene in a mixed cell containing acetylene and methane, with many clear absorption lines around 1526 micrometers. FIG. 3 shows the absorption spectrum of methane ($CH_4$) in the region of 1650 micrometers in a mixed cell containing acetylene and methane, again with distinct absorption lines.

This reference cell is used to calibrate an optical instrument in the following manner, deriving a calibration model from multiple calibration points corresponding to known absorption lines in the absorption cell or cells. According to the first calibration method, a plurality of calibration error measurements are taken, corresponding to a plurality of known wavelengths. An average of these calibration error values is calculated, and that average used as the calibration constant. A weighted average may also be used.

One approach to computing a weighted average first examines the data points and removes any outlying points. This is done by removing points at the extremes which are separated more than an error tolerance from their neighbors. Next, points are collected which are within a specified measurement uncertainty of the minimum and maximum values in the remaining set of points. Those points within the measurement uncertainty of the minimum and maximum are given a weight of 100%; the remaining points are given a weight of 0%. Other statistical approaches may also be used.

This method may be extended by segmenting the wavelength range, and calculating and then using separate constants $c_0$ for each segment.

The second calibration method recognizes that the error properties of the device may not be uniform over its measurement range. In this embodiment, a plurality of calibration error measurements are taken at known wavelengths, producing a plurality of calibration error values. This data is used to fit a higher order correction model. While the preferred embodiment uses a least-squares fit linear model, producing an offset and a slope, higher order corrections such as B-splines may also be used. Using the least-squares linear model, the equation mapping position w onto corrected wavelength $l_c$ becomes:

$$l_c = f(c_0 + a_0, c_1 a_1 w)$$

Given n calibration measurements, i=1..n, producing pairs of points ($w_i$, $v_i$), $c_0$ and $c_1$ may be calculated in the usual fashion as:

$$c_1 = \frac{n\sum_1^n w_i v_i - \left(\sum_1^n w_i\right)\left(\sum_1^n v_i\right)}{n\sum_1^n w_i^2 - \left(\sum_1^n w_i\right)^2}$$

$$c_0 = \frac{\sum_1^n v_i}{n} - c_1 \frac{\sum_1^n w_i}{n}$$

In a further refinement of this approach, the wavelength range of the device is segmented, and separate correction values ($c_0$, $c_1$) are calculated and used for each segment.

Higher order calibration models may also be used, such as quadratic or B-spline models. These may be applied in a segmented or a single span approach.

A particular higher order model of interest may be used when the error is periodic in nature. The error characteristics of a particular system may contain components which are periodic in nature. Standard analytical techniques may be used to fit a periodic function to this error data. It should be noted that if there exists apriori information about the error function, the period or spacing of the calibration points can be less than the Nyquist criteria, and a valid correction function can still be derived from this "under-sampled" case. The resulting function, for example, a Fourier series, is then applied as a correction function. As with other embodiments of the invention, a single function may be used spanning the wavelength range of the device, or the range may be segmented and different fits used for each segment. Indeed, there may be specific wavelength regions where higher accuracy is desired, and others where lower accuracy may be tolerated. These may be accommodated by allowing the use of different correction models in different segments of device operation.

For example, in the critical 1.5 and 1.6 micrometer segments, a high order correction such as a periodic correction function may be used. The wavelength segments adjoining there critical regions could use the linear fit model, and the remaining segments could use a simple single term correction.

When a correction model is calculated over an interval smaller than the operating span of the device, care must be used in extrapolating the results obtained over a small interval over the larger span. In extremes, applying a correction model valid over a small interval may actually increase the error at the extremes. One approach is to only apply the correction model to the range over which it was calculated. A second approach is to apply the correction model over a wider range, determined by the error characteristics of the particular device, for example, allowing it to be applied to predetermined bounds above and below the calculated range. As previously described, outside this extended range, other approaches, such as single term correction, may be applied.

The foregoing detailed description of the present invention is provided for the purpose of illustration and is not intended to be exhaustive or to limit the invention to the precise embodiments disclosed. Accordingly the scope of the present invention is defined by the appended claims.

What is claimed is:

1. A method of calibrating an optical instrument comprising the steps of:
   illuminating a gas reference having a plurality of reference gasses in a single cell with a wideband light source producing a spectrum containing absorption lines,
   performing a plurality of wavelength measurements corresponding to absorption lines of each reference gas,
   deriving a set of error values from the plurality of measurements, and
   deriving a calibration model from the set of error values.

2. The method of claim 1 where the calibration model provides a single calibration constant.

3. The method of claim 1 where the single calibration constant is applied over the measurement range.

4. The method of claim 1 where the single calibration constant is applied over a predetermined range larger than the measurement range.

5. The method of claim 1 where the single calibration constant is applied over the wavelength range of the optical wavelength measurement system.

6. The method of claim 1 where the wavelength range of the optical wavelength measurement system is divided into segments and a calibration constant is derived and applied to each segment.

7. The method of claim 1 where the calibration model provides a single calibration constant computed from a weighted average of the set of error values.

8. The method of claim 7 where the single calibration constant is applied over the wavelength range of the optical wavelength measurement system.

9. The method of claim 7 where the single calibration constant is applied over the measurement range.

10. The method of claim 7 where the single calibration constant is applied over a predetermined range larger than the measurement range.

11. The method of claim 7 where the wavelength range of the optical wavelength measurement system is divided into segments and a calibration constant is derived and applied to each segment.

12. The method of claim 1 where the calibration model provides a linear correction computed from the set of error values.

13. The method of claim 12 where the linear correction is applied over the wavelength range of the optical wavelength measurement system.

14. The method of claim 12 where the linear correction is applied over the measurement range.

15. The method of claim 12 where the linear correction is applied over a predetermined range larger than the measurement range.

16. The method of claim 12 where the wavelength range of the optical wavelength measurement system is divided into segments and the linear correction is derived and applied to each segment.

17. The method of claim 1 where the calibration model provides a higher order correction computed from the set of error values.

18. The method of claim 17 where the higher order correction is applied over the wavelength range of the optical wavelength measurement system.

19. The method of claim 17 where the higher order correction is applied over the measurement range.

20. The method of claim 17 where the higher order correction is applied over a predetermined range larger than the measurement range.

21. The method of claim 17 where the wavelength range of the optical wavelength measurement system is divided into segments and the higher order correction is derived and applied to each segment.

22. The method of claim 1 where the calibration model provides a periodic correction computed from the set of error values.

23. The method of claim 22 where the periodic correction is applied over the wavelength range of the optical wavelength measurement system.

24. The method of claim 22 where the periodic correction is applied over the measurement range.

25. The method of claim 22 where the periodic correction is applied over a predetermined range larger than the measurement range.

26. The method of claim 22 where the wavelength range of the optical wavelength measurement system is divided into segments and the periodic correction is derived and applied to each segment.

27. The method of claim 1 where the wavelength range of the optical wavelength measurement system is divided into segments and different correction models are applied to different segments.

* * * * *